US00PP25255P2

(12) United States Plant Patent
Wain

(10) Patent No.: US PP25,255 P2
(45) Date of Patent: Jan. 27, 2015

(54) ***CHRYSANTHEMUM* PLANT NAMED 'FIMMSUNBRO'**

(50) Latin Name: *Chrysanthemum×morifolium*
Varietal Denomination: Fimmsunbro

(71) Applicant: Peter Wain, Locks Heath (GB)

(72) Inventor: Peter Wain, Locks Heath (GB)

(73) Assignee: Fides B.V., DeLier (NL)

( * ) Notice: Subject to any disclaimer, the term of this patent is extended or adjusted under 35 U.S.C. 154(b) by 130 days.

(21) Appl. No.: 13/815,201

(22) Filed: Feb. 8, 2013

(51) Int. Cl.
*A01H 5/00* (2006.01)

(52) U.S. Cl.
USPC ..... Plt./296

(58) Field of Classification Search
USPC ..... Plt./296
See application file for complete search history.

*Primary Examiner* — Annette Para
(74) *Attorney, Agent, or Firm* — C. A. Whealy

(57) ABSTRACT

A new and distinct cultivar of *Chrysanthemum* plant named 'Fimmsunbro', characterized by its upright to outwardly spreading and uniformly mounded plant habit; freely branching habit; dense and full plant habit; uniform and freely flowering habit; medium-sized decorative inflorescences with orange bronze-colored ray florets; mid-September flowering response under natural season conditions; and good garden performance.

1 Drawing Sheet

Botanical designation: *Chrysanthemum×morifolium.*
Cultivar denomination: 'FIMMSUNBRO'.

BACKGROUND OF THE INVENTION

The present invention relates to a new and distinct *Chrysanthemum* plant, botanically known as *Chrysanthemum× morifolium*, commercially grown as a garden *Chrysanthemum* and hereinafter referred to by the name 'Fimmsunbro'.

The new *Chrysanthemum* plant is a product of a planned breeding program conducted by the Inventor in Fareham, Hampshire, United Kingdom. The objective of the breeding program is to create new early-flowering garden *Chrysanthemum* plants with numerous attractive inflorescences.

The new *Chrysanthemum* plant originated from a cross-pollination made in January, 2007 by the Inventor in Fareham, Hampshire, United Kingdom of a proprietary selection of *Chrysanthemum×morifolium* identified as code number 82660, not patented, as the female, or seed, parent with a proprietary selection of *Chrysanthemum×morifolium* identified as code number 3044, not patented, as the male, or pollen, parent. The new *Chrysanthemum* plant was discovered and selected by the Inventor as a single flowering plant from within the progeny of the stated cross-pollination in a controlled greenhouse environment in Fareham, Hampshire, United Kingdom in September, 2007.

Asexual reproduction of the new *Chrysanthemum* by terminal vegetative cuttings was first conducted in Fareham, Hampshire, United Kingdom in December, 2007. Asexual reproduction by terminal vegetative cuttings has shown that the unique features of this new *Chrysanthemum* are stable and reproduced true to type in successive generations.

SUMMARY OF THE INVENTION

Plants of the new *Chrysanthemum* have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Fimmsunbro'. These characteristics in combination distinguish 'Fimmsunbro' as a new and distinct *Chrysanthemum* plant:

1. Upright to outwardly spreading and uniformly mounded plant habit.
2. Freely branching habit; dense and full plant habit.
3. Uniform and freely flowering habit.
4. Medium-sized decorative inflorescences with orange bronze-colored ray florets.
5. Plants flower under natural season conditions during the third week of September in the United Kingdom.
6. Good garden performance.

Plants of the new *Chrysanthemum* can be compared to plants of the female parent selection. Plants of the new *Chrysanthemum* differ from plants of the female parent selection, in the following characteristics:

1. Plants of the new *Chrysanthemum* have larger inflorescences than plants of the female parent selection.
2. Plants of the new *Chrysanthemum* and the female parent selection differ in ray floret color as plants of the female parent selection have yellow-colored ray florets.

Plants of the new *Chrysanthemum* can be compared to plants of the male parent selection. Plants of the new *Chrysanthemum* differ from plants of the male parent selection, in the following characteristics:

1. Plants of the new *Chrysanthemum* have smaller inflorescences than plants of the male parent selection.
2. Plants of the new *Chrysanthemum* and the male parent selection differ in ray floret color as plants of the male parent selection have light red-colored ray florets.

Plants of the new *Chrysanthemum* can be compared to plants of *Chrysanthemum×morifolium* 'Conaco Bronze', not patented. In side-by-side comparisons conducted in Fareham, Hampshire, United Kingdom, plants of the new *Chrysanthemum* differed from plants of 'Conaco Bronze' in the following characteristics:

1. Plants of the new *Chrysanthemum* flowered 13 days earlier than plants of 'Conaco Bronze' under photoinductive conditions.
2. Plants of the new *Chrysanthemum* had smaller inflorescences than plants of 'Conaco Bronze'.
3. Plants of the new *Chrysanthemum* and 'Conaco Bronze' differed in ray floret color as plants of 'Conaco Bronze' had dark bronze-colored ray florets.

BRIEF DESCRIPTION OF THE PHOTOGRAPH

The accompanying photograph illustrates the overall appearance of the new *Chrysanthemum* showing the colors as true as it is reasonably possible to obtain in colored reproductions of this type. Colors in the photograph may differ slightly from the color values cited in the detailed botanical description which accurately describe the colors of the new *Chrysanthemum*. The photograph comprises a top perspective view of a typical flowering plant of 'Fimmsunbro' grown in a container.

DETAILED BOTANICAL DESCRIPTION

The aforementioned photograph and following observations and measurements describe plants grown during the late summer and early autumn in 19-cm containers in an outdoor nursery in Fareham, Hampshire, United Kingdom and under cultural practices typical of commercial garden *Chrysanthemum* production. During the production of the plants, day temperatures ranged from 10° C. to 25° C., night temperatures ranged from 5° C. to 15° C. and light levels ranged from 400 to 2,500 joules. Plants were pinched one time and were about 14 weeks old when the photograph and detailed description were taken. In the following description, color references are made to The Royal Horticultural Society Colour Chart, Fifth Edition, except where general terms of ordinary dictionary significance are used.

Botanical classification: *Chrysanthemum×morifolium* 'Fimmsunbro'.

Parentage:

*Female, or seed, parent*.—Proprietary selection of *Chrysanthemum×morifolium* identified as code number 82660, not patented.

*Male, or pollen, parent*.—Proprietary selection of *Chrysanthemum×morifolium* identified as code number 3044, not patented.

Propagation:

*Type*.—Terminal vegetative cuttings.

*Time to initiate roots, summer*.—About ten days at temperatures of about 21° C.

*Time to initiate roots, winter*.—About twelve days at temperatures of about 21° C.

*Time to produce a rooted young plant, summer*.—About three weeks at temperatures of about 21° C.

*Time to produce a rooted young plant, winter*.—About four weeks at temperatures of about 21° C.

*Root description*.—Fine, fibrous; light brown in color.

*Rooting habit*.—Freely branching; medium density to dense.

Plant description:

*Plant and growth habit*.—Herbaceous decorative-type garden *Chrysanthemum*; stems upright to outwardly spreading giving a uniformly mounded appearance to the plant; numerous lateral branches and relatively short internodes, dense and full plant habit; moderately vigorous growth habit.

*Plant height*.—About 30 cm.

*Plant width*.—About 49 cm.

*Branching habit*.—Freely branching habit, about twelve lateral branches develop after removal of terminal apex (pinching); each primary lateral with numerous secondary laterals.

*Lateral branches*.—Length: About 25.5 cm. Diameter: About 7 mm. Internode length: About 6 mm. Strength: Strong. Aspect: About 80° from stem. Texture: Fine pubescence. Color: Close to N199A.

*Leaves*.—Arrangement: Alternate or occasionally opposite, simple. Length: About 4.5 cm. Width: About 2.3 cm. Shape: Palmately-lobed; roughly ovate. Apex: Acuminate and mucronate. Base: Obtuse with truncate tendencies. Margin: Palmately lobed, sinuses between lateral lobes parallel to divergent; slightly dentate. Texture, upper surface: Fine pubescence, sparse. Texture, lower surface: Fine pubescence; veins prominent. Color: Developing leaves, upper surface: Close to 147A. Developing leaves, lower surface: Close to N138B. Fully expanded leaves, upper surface: Close to N137B; venation, close to 137D. Fully expanded leaves, lower surface: Close to N138B; venation, close to N138B. Petiole: Length: About 1 cm. Diameter: About 2 mm. Texture, upper and lower surfaces: Fine pubescence. Color, upper surface: Close to N137A. Color, lower surface: Close to N138B.

Inflorescence description:

*Form and flowering habit*.—Decorative inflorescence form with oblanceolate-shaped ray florets; inflorescences borne on terminals above and beyond the foliar plane; disc and ray florets arranged acropetally on a capitulum; freely flowering habit with about 75 inflorescences developing per lateral branch and about 2,700 inflorescences developing per plant.

*Fragrance*.—Slightly fragrant; pungent, herbaceous.

*Flowering response*.—Early flowering habit, plants exposed to natural season conditions begin flowering the third week of September in the United Kingdom; with photoinductive treatments, response time is about 33 days.

*Inflorescence longevity*.—Inflorescences maintain good color and substance for about three to five weeks on the plant; inflorescences persistent.

*Inflorescence buds*.—Height: About 5 mm. Diameter: About 5 mm. Shape: Globular. Color: Close to 137A.

*Inflorescence height*.—About 2.1 cm.

*Inflorescence diameter*.—About 3.5 cm.

*Disc diameter*.—About 3 mm.

*Receptacles*.—Height: About 3 mm. Diameter: About 3 mm. Shape: Ovoid. Color: Close to 145C.

*Ray florets*.—Orientation: Initially upright, then about 45° from vertical. Length: About 1.9 cm. Width: About 5 mm. Shape: Oblanceolate. Apex: Emarginate. Base: Fused into a short tube. Margin: Entire. Texture, upper and lower surfaces: Smooth, glabrous. Number of ray florets per inflorescence: About 89 arranged in about five whorls. Color: When opening, upper surface: More bronze than 34A. When opening, lower surface: Close to 29A. Fully opened, upper surface: Close to N34B; color becoming closer to 34C with development. Fully opened, lower surface: Close to 29B; color becoming closer to 29C with development.

*Disc florets*.—Shape: Tubular, elongated. Length: About 6 mm. Diameter: About 1 mm. Number of disc florets per inflorescence: About eight. Color, immature and mature: Apex: Close to 13B. Mid-section: Close to 1C. Base: Close to 155D.

*Phyllaries*.—Number of phyllaries per inflorescence: About 21 arranged in about four whorls. Length: About 7 mm. Width: About 3 mm. Shape: Ovate. Apex: Acute to obtuse. Base: Rounded to truncate, fused. Margin: Entire. Texture, upper surface: Smooth, glabrous; waxy. Texture, lower surface: Fine pubescence; waxy. Color, upper surface: Close to 144A. Color, lower surface: Close to 143A.

*Peduncles*.—Length, terminal peduncle: About 3.7 cm. Diameter, terminal peduncle: About 1.5 mm. Angle: Erect to about 15° from vertical. Strength: Weak; flexible. Texture: Fine pubescence. Color: Close to 138A.

*Reproductive organs*.—Androecium: None observed. Gynoecium (present on ray and disc florets): Pistil length: About 5 mm. Stigma shape: Bi-parted. Stigma color: Close to 12A. Style length: About 3 mm. Style color: Close to 4B. Ovary color: Close to NN155C.

*Seeds and fruits*.—Seed and fruit production has not been observed on plants of the new *Chrysanthemum*.

Disease & pest resistance: Resistance to pathogens and pests common to *Chrysanthemum* plants has not been observed on plants of the new *Chrysanthemum* grown under commercial conditions.

Garden performance: Plants of the new *Chrysanthemum* have demonstrated good garden performance and to tolerate temperatures from about 0° C. to about 35° C.

It is claimed:

1. A new and distinct *Chrysanthemum* plant named 'Fimmsunbro' as illustrated and described.

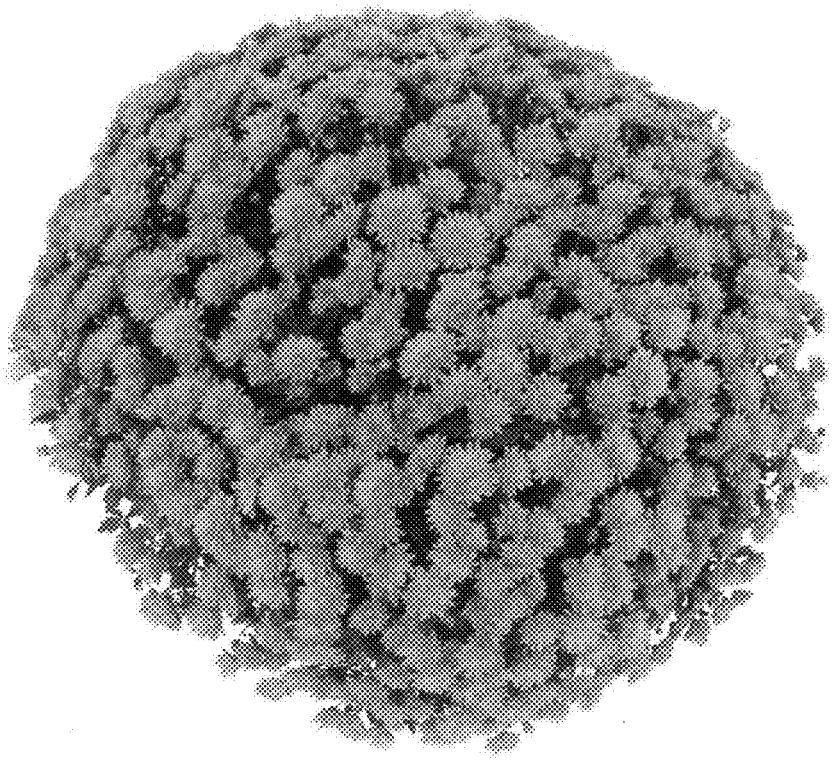

* * * * *